(12) United States Patent
Casiraghi et al.

(10) Patent No.: US 8,933,142 B2
(45) Date of Patent: Jan. 13, 2015

(54) LOW-EXTRACTABLE THIOXANTHONES

(75) Inventors: Angelo Casiraghi, Milan (IT); Enzo Meneguzzo, Sesto Calende (IT); Gabriele Norcini, Comabbio (IT); Elena Bellotti, Marnate (IT); Giovanni Floridi, Novara (IT); Giuseppe Li Bassi, Gavirate (IT)

(73) Assignee: Lamberti Spa, Albizzate (VA) (IT)

( * ) Notice: Subject to any disclaimer, the term of this patent is extended or adjusted under 35 U.S.C. 154(b) by 5 days.

(21) Appl. No.: 13/884,507

(22) PCT Filed: Nov. 7, 2011

(86) PCT No.: PCT/EP2011/069514
§ 371 (c)(1),
(2), (4) Date: May 9, 2013

(87) PCT Pub. No.: WO2012/062692
PCT Pub. Date: May 18, 2012

(65) Prior Publication Data
US 2013/0237628 A1    Sep. 12, 2013

(30) Foreign Application Priority Data
Nov. 10, 2010 (IT) .............................. VA2010A0082

(51) Int. Cl.
| | |
|---|---|
| *B41M 5/28* | (2006.01) |
| *A61L 27/34* | (2006.01) |
| *C08F 2/50* | (2006.01) |
| *B29C 71/04* | (2006.01) |
| *A61L 2/08* | (2006.01) |
| *A61L 24/00* | (2006.01) |
| *C08F 2/46* | (2006.01) |
| *C08G 61/04* | (2006.01) |
| *C08J 3/28* | (2006.01) |
| *C07D 335/16* | (2006.01) |

(52) U.S. Cl.
CPC ................. *C08J 3/28* (2013.01); *C07D 335/16* (2013.01); *C08F 2/50* (2013.01)
USPC ...... 522/53; 522/49; 522/6; 522/71; 522/189; 522/184; 522/1; 520/1

(58) Field of Classification Search
CPC ........... C07D 337/00; C08F 2/46; C08F 2/50; C08J 3/28
USPC ............. 522/53, 49, 6, 71, 189, 184, 1; 520/1
See application file for complete search history.

(56) References Cited

U.S. PATENT DOCUMENTS

| | | | |
|---|---|---|---|
| 3,904,647 A | 9/1975 | Pfister et al. | |
| 4,348,530 A | * 9/1982 | Kvita et al. ..................... | 549/27 |
| 4,505,794 A | * 3/1985 | Kvita et al. ..................... | 522/14 |

FOREIGN PATENT DOCUMENTS

| | | | |
|---|---|---|---|
| CN | 1660837 A | | 8/2005 |
| EP | 2007/017298 | * | 2/2007 |

* cited by examiner

*Primary Examiner* — Ling Choi
*Assistant Examiner* — Jessica E Whiteley
(74) *Attorney, Agent, or Firm* — Mossman, Kumar & Tyler PC

(57) ABSTRACT

3-Esters and 3-amides of thioxanthone bearing alkyl chains of appropriate length and can be used as photoinitiators or sensitizers in photopolymerizable systems, in particular for the preparation of coatings compatible with the food use.

6 Claims, No Drawings

LOW-EXTRACTABLE THIOXANTHONES

TECHNICAL FIELD

The present invention relates to substituted derivatives of thioxanthone which can be used as photoinitiators and sensitizers, to photopolymerizable compositions comprising said derivatives and to a method for coating a substrate applying said compositions.

DESCRIPTION OF THE INVENTION

Photopolymerizable systems contain photoinitiators that possess in the molecule a functional group which, by exposure to light radiation of appropriate wavelength, generate radicals able to initiate the polymerization.

It is well known that photoinitiators must meet strict requirements of low toxicity, low volatility, low extractability (low migration) and low odor, and must be highly compatible with the photopolymerizable system. These properties are essential in the food-packaging sector, in particular for the inks used for package printing.

Contamination from the photoinitiator can modify the organoleptic characteristics of food and is forbidden by the current legislative regulations.

Moreover, in the photopolymerizable systems, it is essential to reduce the migration of compounds that can cause undesired effects, such as loss of adhesion to the substrate.

It is known that isopropyl thioxanthone (ITX) and its derivatives are very good photoinitiators and sensitizers for pigmented systems; however ITX is not suitable for the food packaging, since it has the tendency to migrate from the photopolymerized coating, in particular from the printing inks into the packaged food product, as a consequence of indirect contact.

Generally, the structural modifications aimed at avoiding migration of the derivatives of thioxanthone are based on the introduction of unsaturated copolymerizable groups, as described for example in U.S. Pat. No. 4,348,530, or on the synthesis of oligomeric derivatives of thioxanthone, such as OMNIPOL TX® (IGM Resins) or the products described in CN 1660837.

Unfortunately, the chemical reactivity of the these derivatives of thioxanthone turn out to be always inferior than ITX. In particular, the oligomeric derivatives are definitely less reactive than ITX.

It is known from the literature (Journal of Photochemistry, 35 (1986), 353-356) that some high molecular weight derivatives of thioxanthone, opportunely substituted, can have a reactivity comparable to the reactivity of ITX. In particular, the presence of a electron-attractive group in position 1 or 3 of thioxanthone produces a bathochromic shift in the absorption of light which causes an increase of reactivity. Such increase of reactivity compensates the increase of molecular weight that, using the same amount by weight of photoiniziators, would reduce the applicative performance of the photopolymerizable composition.

U.S. Pat. No. 4,505,794 describes the preparation of several esters and amides of thioxanthone substituted in positions 1 and 3 in order to improve their solubility in formulates in comparison with ITX. In particular, the methyl ester and the N-isopropyl amide of thioxanthone in position 1 are indicated as the products with high activity, while only the ethyl and n-butyl esters, but no amide, are described as substituents in position 3.

We have now observed that the introduction of an ester or an amide in position 1 or 3 is not equivalent from the point of view of their reactivity and that, in particular, the derivatives substituted in position 3 are sensibly more active. Surprisingly, moreover, the overall performance (i.e. reactivity, solubility and compatibility with photopolymerizable systems and low extractability) of the esters, thioesters and amides in 3 of thioxanthone is strongly dependent from the length of the alkyl chain bonded to the oxygen or nitrogen. These chains, when appropriately selected, reduce or eliminate the extractability of the derivatives of thioxanthone in formulates, thus maintaining superior compatibility and reactivity. The object of the present invention are therefore specific esters and amides of thioxanthone, which bear alkyl chains of appropriate length and can be used as photoinitiators or sensitizers in photopolymerizable systems, in particular for the preparation of coatings compatible with the food use.

By sensitizer we mean a compound that, through a process of energy transfer, activates the photoinitiator at a wavelength where the photoinitiator alone would not be reactive.

DESCRIPTION OF THE INVENTION

It is an object of the present invention a photopolymerizable composition comprising from 70 to 99.9% by weight, preferably from 70 to 98.9% by weight, of at least one photopolymerizable compound and from 0.1 to 20% by weight, preferably from 0.2 to 7% by weight, of at least one derivative of thioxanthone of formula I

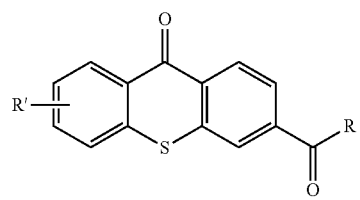

where
R is $OR_1$, $SR_1$ or $NR_2R_3$;
R' is hydrogen or a linear or branched alkyl chain $C_1$-$C_4$;
$R_1$ is a linear or branched alkyl chain $C_8$-$C_{16}$;
$R_2$ and $R_3$ can be equal or different and are a linear or branched chain $C_4$-$C_8$ or can be combined in order to form a ring, optionally substituted, with 5 or 6 members and containing up to two further heteroatoms.

It is a further object of the present invention a derivative of thioxanthone of formula I

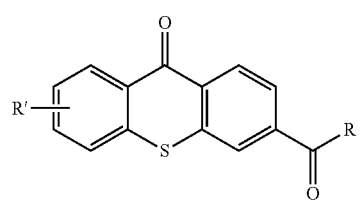

wherein R is $OR_1$ and $R_1$ is a $C_{12}$ linear alkyl chain, or R is $NR_2R_3$ and $R_2$ and $R_3$ are isobutyl, and R' is hydrogen or R' is in the position 7 and is methyl.

Another object of the invention is the use of the above described photopolymerizable compositions in the preparation of food packaging, in particular as photocrosslinkable pigmented inks.

A further embodiment of the present invention is a method for coating a substrate comprising the following steps:

I. applying onto said substrate the above photopolymerizable composition according to the invention in such an amount to obtain, after polymerization, a coating with a thickness comprised between 0.2 and 100 microns;
II. photopolymerizing the composition with a light source having emission bands in the UV-Visible region.

It is finally an object of the invention the use of the substrates coated according to the method described above in the preparation of food packaging.

DETAILED DESCRIPTION OF THE INVENTION

For the preparation of the photopolymerizable composition, the derivatives of thioxanthone of formula I in which R is OR, or $NR_2R_3$ are preferred. Preferably R' is hydrogen or R' is in position 7 and is methyl.

The derivatives in which $R_1$ is a linear $C_{12}$ chain and $R_2$ and $R_3$ are both a isobutyl group are particularly preferred.

The derivatives of thioxanthone of formula I according to the invention can be prepared according conventional methods known to the experts in the art. In particular they can be prepared cyclizing compounds of formula II or II'

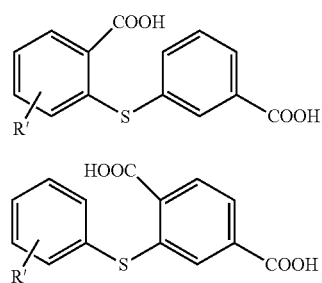

in which R' it has the same meaning of formula I, according the scheme:

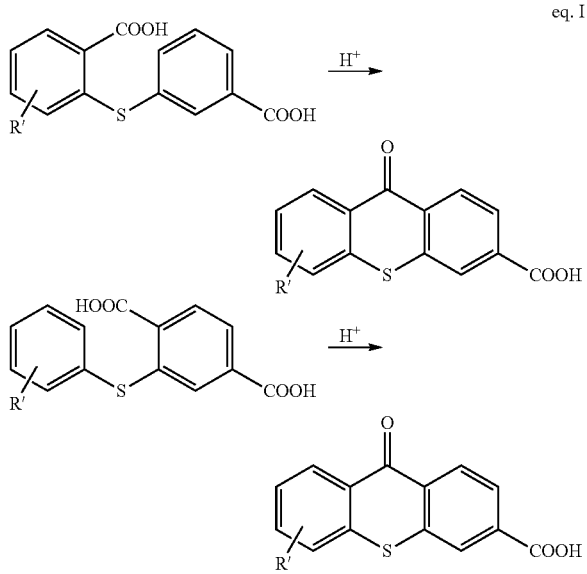

The cyclization of compounds can be obtained in the presence of protic acids or Lewis' acids at temperatures comprised between −50° C. and 150° C. and preferably between −10° C. and 50 C.° for a period of time adequate to complete the reaction, which is normally comprised between 15 min and 2 hours.

Examples of suitable protic acids are concentrated sulfuric acid, chlorosulfonic acid, methanesulfonic acid and polyphosphoric acid. Examples of Lewis' acid are aluminum trichloride, aluminum tribromide, boron trifluoride, zinc chloride and iron trichloride.

The compounds of formula II can be prepared by reacting a compound of formula III or IV, or one of their derivatives, with a compound of formula V

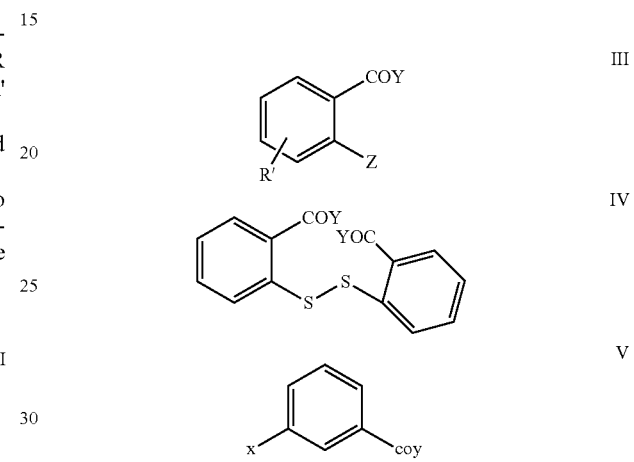

In the compounds III and IV R' has same meaning of formula I, Y can be OMe, OEt, Cl, Br or OY' where Y' can be hydrogen, an alkaline or alkaline-earth metal, and Z can be a thiol group, one of its salts with an alkaline or alkaline-earth metal, or one of its chlorinated derivatives.

In the compound of formula V the group X is a good leaving group, for example an atom of Cl, Br, and Y assumes the same meaning as described before.

The reaction is carried out at a temperature comprised between 0 and 300° C., but preferably between 50 and 200° C. in the presence of an organic solvent, preferably aprotic solvents such as dimethyl sulfoxide, N,N-dimethyl formamide, N,N dimethyl acetamide, N-methyl pyrrolidone, and in the presence of copper powder and anhydrous potassium carbonate, as described in U.S. Pat. No. 3,904,647, according to the reaction scheme:

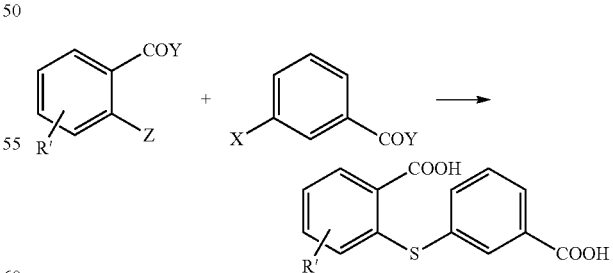

Examples of compound III that can be used are thiosalicylic acid and its derivatives, while examples of compound IV are dithiosalicylic acid and its derivatives.

The compounds of formula II' can be obtained, as described in U.S. Pat. No. 4,505,794, reacting a compound of formula VI, or a its derivative, with a formula compound VII,

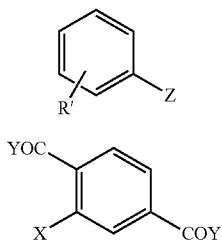

VI

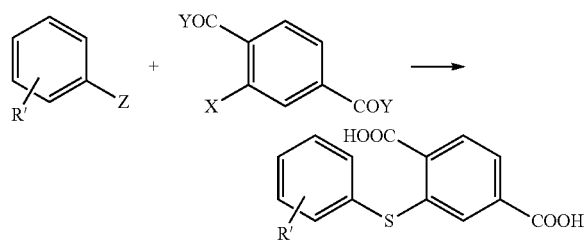

VII in which R', X, Y and Z have the meaning as previously described, according to the scheme:

The formation of the diphenyl thioether may be obtained by reacting a salt of a thiol group with an alkaline-earth metal with a nitro-benzene substituted in a high-boiling polar organic solvent, such as those indicated before, or a mixture thereof. The mixture is maintained at a temperature preferably comprised between 50° C. and 150° C. for a period of time sufficient to complete the reaction, usually between 2 and 7 hours.

The preparation of the ester or the thioester of formula I can be carried out by reacting the carboxylic acid obtained in Eq. I or one of its derivatives, as an example its acyl chloride, with an alcohol or a thiol, optionally in organic solvent such as toluene or methylene chloride, but the reaction is preferably carried out using an excess of the alcohol or thiol at the reflux temperature of the reaction mass. The use of carboxylic acid requires the presence of a dehydrating agent such as gaseous HCl or concentrated sulphuric acid, while the use of an acyl chloride requires the presence of an organic base such as triethyl amine or pyridine.

The secondary amides of formula I are obtained by reacting the carboxylic acids obtained in eq. I or one of its derivatives with the corresponding secondary amine in a suitable inert solvent like methylene chloride, toluene, dioxane, optionally in the presence of an excess of the amine at a temperature comprised between 20 and 100° C.

The conversion of the acid obtained in eq. I in one of its derivatives, in particular in an acyl chloride, can be obtained using chlorination agents such as thionyl chloride, oxalyl chloride, phosphorus pentachloride, optionally in the presence of an inert solvent, employing an excess of the chlorination agent.

The photopolymerizable compositions of the invention can also conveniently include a coinitiator, which is a molecule that acts as hydrogen donor that increases the polymerization rate. The coinitiators are known in the art and are typically alcohols, thiols, amines or ethers that have an available hydrogen, bonded to a carbon adjacent to the heteroatom. Such coinitiators are generally present in an amount comprised between 0.2 and 15% by weight, preferably from 0.2 to 8% by weight. Suitable coinitiators include, but are not limited to, aliphatic, cycloaliphatic, aromatic, aryl-aliphatic, heterocyclic, oligomeric or polymeric amines. They can be primary, secondary or tertiary amines, for example butyl amine, dibutyl amine, tributyl amine, cyclohexyl amine, benzyldimethyl amine, di-cyclohexyl amine, triethyl amine, phenyl-diethanol amine, pyperidine, pyperazine, morpholine, pyridine, quinoline, esters of dimethylamino benzoic acid, Michler's ketone (4,4'-bis-dimethyl aminobenzophenone). For food packaging, it is advisable to use non-extractable coinitiators, for example Esacure A 198 (bis-N,N-[4-dimethylaminobenzoyl) oxyethylen-1-yl]-methylamine) from Lamberti S.p.A., IT.

The photopolymerizable composition of the invention can also conveniently include other photoinitiators. Examples of photoinitiators which can be used in combination with the derivatives of thioxanthone of formula I are benzophenones, ketosulfones, $\alpha$-aminoketones, benzoin and benzoin ethers, benzil ketals, $\alpha$-hydroxyketones.

Preferred photoinitiators, suitable for food packaging, belong to the classes of $\alpha$-hydroxyketones, ketosulfones and bi-functional photoinitiators, for example Esacure 1001 and Esacure ONE (commercialized by Lamberti S.p.A., IT).

Additional photoinitiators can be added to the photopolymerizable composition of the invention in an amount comprised between 0.5 and 10% by weight, preferably between 1 and 5% by weight.

In a particularly preferred embodiment of the invention the derivatives of thioxanthone of formula I are used as sentitizers of sensitizable photoinitiators in photopolymerizable compositions.

In this case, the photopolymerizable composition comprises from 70 to 98.9% by weight of at least one photopolymerizable compound, from 0.1 to 5% by weight of at least one thioxanthone derivative of formula I, from 1 to a 10% by weight at least one sensitizable photoinitiator, for example a ketosulfone or an $\alpha$-aminoketone and, possibly, a coinitiator The preferred sensitizable photoinitiator is 1-[4-[(4-benzoyl-phenyl)-thio]-phenyl],2-methyl, 2-[(4-methyl-phenyl)-sulfonyl]-propan-1-one (Esacure 1001).

In the above particularly preferred compositions, the coinitiator is generally present in an amount comprised between 0.2 and 15% by weight, preferably from 0.2 to 8% by weight.

By photopolymerizable compounds we mean a monomer, oligomer, prepolymer, typically ethylenically unsaturated compounds or mixtures thereof, capable of undergoing radical polymerization. Also monomer combinations, oligomers and prepolymers with different degrees of functionality can be used.

The monomers and oligomers of the photopolymerizable composition of the present invention can be chosen between vinyl ethers; N-vinyl pyrrolidone; mono- and poly-functional allyl ethers such as trimethylol propane diallyl ether; styrenes and alpha-methyl styrenes; esters of (meth)acrylic acid with aliphatic alcohol, glycols, polyhydroxylated compounds such as pentaerythritol or trimethylol propane; ester of vinyl alcohol with acrylic or aliphatic acids, derivatives of fumaric and maleic acids.

Suitable oligomers or prepolymers for the present invention comprise, for example, polyesters, polyacrylates, polyurethanes, epoxy resins, polyethers with acrylic, maleic or fumaric functionalities.

Besides the above-mentioned compounds, other components normally used in the field and known to the experts in the art can be added to the photopolymerizable composition of the invention. For example, thermal stabilizers, photo-oxidation stabilizers, anti-oxidants, fillers, dispersants, pigments, coloring and/or opacifying substances and other additives of general use. Others components of the photopolymerizable composition of the invention can be non-photopolymerizable polymers present as chemically inert substances, as an example nitrocellulose, polyacrylic esters, polyolefins etc. Preferred components are those with reactivity and toxicity characteristics suitable for food packaging. The derivatives of the thioxanthone of formula I work both in transparent photopolymerizable compositions and in non-transparent or pigmented compositions and are useful for example also for the preparation of photocrosslinkable inks.

Thioxantone derivatives of formula I wherein R is R is $OR_1$ and $R_1$ is a $C_{12}$ linear alkyl chain, or R is $NR_2R_3$ and $R_2$ and $R_3$ are isobutyl, and R' is hydrogen or R' is in the position 7 and is methyl are particularly suitable for the preparation of pigmented photocrosslinkable inks, especially for food packages.

The compositions claimed in the present invention are useful in the treatment of metallic, wood, paper and plastic surfaces.

Examples of suitable light source for photopolymerizing the compositions of the invention are mercury or super actinic lamps; metal-halogen, i.e. iron iodide, or excimers lamps; LED with emission bands in the UV-Visible region and in particular between 180 and 450 nm or laser emitting at an adequate wavelength (for example 405 nm) and with a good power. Among the suitable light sources, solar light and other sources which emit electromagnetic radiation with wavelength from 180 nm to the IR zone can be also included.

The photopolymerizable composition of the present invention is in general particularly suitable for the preparation of coatings compatible with the food contact use and in particular for the preparation of photopolymerizable inks used in food packaging.

Examples of preparation of derivatives of thioxanthone of formula I and photopolymerizable compositions according to the invention, only for illustrative purpose and not limitative, are reported in the following paragraphs.

EXAMPLES

Preparation of
7-methyl-9-oxo-9H-thioxanthene-3-carboxylic acid 10 g (80.65 mmoles) of 4-methylbenzenethiol are added to a three-neck flask equipped with a thermometer and a condenser and dissolved in 50 cc of dimethyl formamide. 3.39 g (84.75 mmoles) of finely ground sodium hydroxide are added and the solution is left to rest at room temperature under constant stirring for half hour. Then, 18.89 g (79.04 mmoles) of dimethyl 2-nitrobenzene-1,4-dicarboxylate are added maintaining the temperature at 75° C. for 1.5 hours. Once the reaction is terminated, the mixture is cooled down and 100 ml of water are added. The precipitate formed is filtered and stirred for 1 hour under refluxing with a solution of 9.33 g (16.67 mmoles) of potassium hydroxide in 120 ml of methanol.

The mixture is cooled and poured in water containing activated carbon for decoloration, after one hour of stirring the mixture is filtered on celite. The organic solvent is distilled on a rotary evaporator and the residue is washed with methylene chloride (twice). The aqueous phase is then acidified with hydrochloric acid 37%. The precipitate obtained is filtered on a buckner, washed with water and dried in a vacuum oven to a final yield of 21.72 g (yield: 95%) of 2-(p-tolylthio)benzene-1,4-dicarboxylic acid as a white solid The 2-(p-tolylthio)benzene-1,4-dicarboxylic acid is transferred slowly to a flask, containing 100 ml of chlorosulfonic acid. The temperature is maintained between the 5 and 10° C. with an ice-bath. At the end of the addition, the solution is left to rest for maturation and after 1 hour is poured in water and ice. The precipitate is filtered, washed with water and dried in a vacuum oven obtaining 19.69 g (yield: 96.7%) of 7-methyl-9-oxo-thioxanthene-3-carboxylic acid as a yellow solid. Melting point>250° C.

Preparation of
7-methyl-9-oxo-thioxanthene-3-carbonyl chloride 8 g of 7-methyl-9-oxo-thioxanthene-3-carboxylic acid are suspended in 100 ml of toluene containing 7 drops of DMF and 7.2 g of thionyl chloride. The temperature is kept at 75-80° C. and the solution is stirred for approximately 1 hour. The reaction is completed by adding a further 2 g of $SOCl_2$ and stirring for another ½ hour.

The solvent is distilled in a rotary evaporator and the residue is dissolved in $CH_2Cl_2$, obtaining a yellow solution used as such in the following reactions.

Example 1

Synthesis of dodecyl-7-methyl-9-oxo-9H-thioxanthene-3-carboxylate

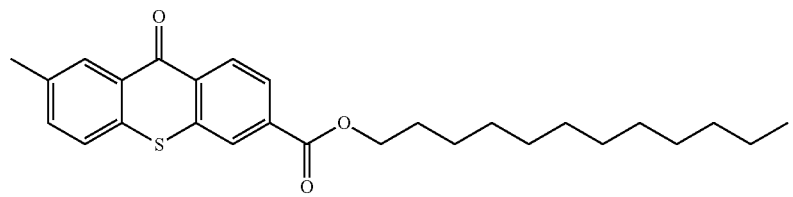 [SMILES: CCCCCCCCCCCCOC(=O)c1ccc2c(=O)c3cc(C)ccc3sc2c1]

1.5 g (8.06 mmoles) of dodecan-1-ol and 1.0 g (9.90 mmoles) of triethyl amine are added to a $CH_2Cl_2$ solution containing 2.26 g (7.41 mmoles) of 7-methyl 9-oxo-thioxanthene-3-carbonyl chloride. After approximately 1 hour at room temperature under stirring, the mixture is poured in water, the organic phase is separated and washed again with water. The organic phase is then separated, dehydrated and after purification on a flash column ($SiO_2$— eluent: $CH_2Cl_2$: AcOEt 8:2) it is dried, obtaining 1.62 g (49.8%) of a yellow solid with the following spectral properties:

$^1$H-NMR ($CDCl_3$): δ (ppm): 8.65 (d, 1H); 8.4 (s, 1H); 8.2 (s, 1H); 8.0 (d, 1H); 7.45 (m, 2H); 4.35 (t, 2H); 2.45 (s, 3H); 1.8 (m, 2H); 1.5-1.15 (bm, 18H); 0.85 (t, 3H).

Example 2

(Comparative). Synthesis of pentyl 7-methyl-9-oxo-9H-thioxanthene-3-carboxylate

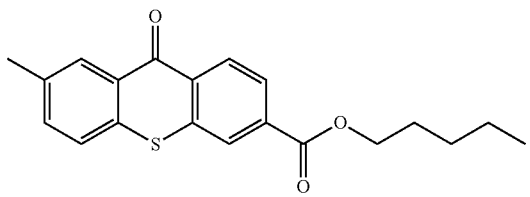 [SMILES: CCCCCOC(=O)c1ccc2c(=O)c3cc(C)ccc3sc2c1]

1.0 g (11.36 mmoles) of pentan-1-ol (containing also -pentan-2-ol) and 1.0 g (9.90 mmoles) of triethyl amine chloride are added to the $CH_2Cl_2$ solution containing 2.26 g (7.41 mmoles) of 7-methyl-9-oxo-thioxanthene-3-carbonyl chloride. After approximately 1 hour at room temperature under stirring, the mixture is poured in water, the organic phase is separated and washed again with water. The organic phase is then separated, dehydrated and after purification on a flash column ($SiO_2$— eluent: $CH_2Cl_2$:AcOEt 8:2) it is dried, obtaining 1.74 g (71.6%) of a yellow solid with the following spectral properties:

$^1$H-NMR (CDCl$_3$): δ (ppm): 8.65 (d, 1H); 8.4 (s, 1H); 8.2 (s, 1H); 8.0 (d, 1H); 7.45 (m, 2H); 4.35 (t, 2H); 2.45 (s, 3H); 1.8 (t, 2H); 1.4 (m, 4H); 0.95 (t, 3H).

Example 3

(Comparative). Synthesis of methyl 7-methyl-9-oxo-9H-thioxanthene-3-carboxylate

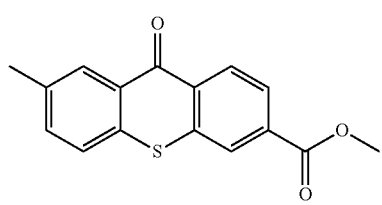

1.0 g (31.3 mmoles) of methanol and 1.0 g (9.90 mmoles) of triethyl amine are added to the $CH_2Cl_2$ solution containing 2.26 g (7.41 mmoles) of 7-methyl 9-oxo-thioxanthene-3-carbonyl chloride. After approximately 1 hour at room temperature under stirring, the mixture is poured in water, the organic phase is separated and washed again with water. The organic phase is then separated, dehydrated and after purification on a flash column ($SiO_2$— eluent: $CH_2Cl_2$:AcOEt 8:2) it is dried, obtaining 1.22 g (58%) of a yellow solid with the following spectral properties:

$^1$H-NMR (CDCl$_3$): δ (ppm): 8.65 (d, 1H2H); 8.4 (s, 1H); 8.25 (s, 1H); 8.0 (s, 1H); 7.45 (m, 2H); 4.0 (s, 3H); 2.5 (s, 3H).

Example 4

(Comparative). Synthesis of allyl 7-methyl-9-oxo-9H-thioxanthene-3-carboxylate

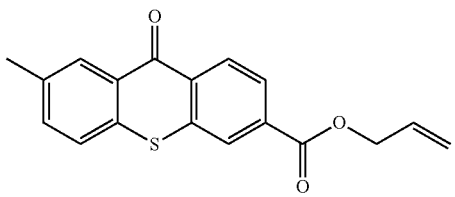 [SMILES: C=CCOC(=O)c1ccc2c(=O)c3cc(C)ccc3sc2c1]

1.13 g (19.4 mmoles) of prop-2-en-1-ol and 2.06 g (20.4 mmoles) of triethyl amine are added to the $CH_2Cl_2$ solution containing 5.34 g (18.5 mmoles) of 7-methyl-9-oxo-thioxanthene-3-carbonyl chloride. After approximately 1 hour at room temperature under stirring, the mixture is poured in water, the organic phase is separated and washed again with water. The organic phase is then separated, dehydrated and dried after purification on a flash column ($SiO_2$— eluent: $CH_2O_2$). 3.02 g (52.6%) of a yellow solid with the following spectral properties are obtained:

$^1$H-NMR (CDCl$_3$): δ (ppm): 8.65 (d, 1H); 8.35 (s, 1H); 8.2 (s, 1H); 8.0 (d, 1H); 7.45 (m, 2H); 6.05 (m, 1H); 5.5-5.3 (dd, 2H); 4.85 (d, 2H); 2.45 (s, 3H).

Example 5

Synthesis of N,N-disobutyl 7-methyl-9-oxo-9H-thioxanthene-3-carboxamide

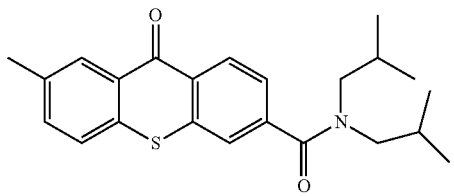 [SMILES: Cc1ccc2sc3cc(C(=O)N(CC(C)C)CC(C)C)ccc3c(=O)c2c1]

A solution of 5.0 g (38.8 mmoles) of diisobutyl amine and 5.0 g (49.5 mmoles) of triethyl amine in 40 cc of $CH_2Cl_2$ is poured drop by drop in the $CH_2Cl_2$ solution containing 7.47 g (25.9 mmoles) of 7-methyl 9-oxo-thioxanthene-3-carbonyl chloride. After approximately 1 hour at room temperature under stirring, the mixture is poured in water, the organic phase is separated and washed again with water. The organic phase is then separated, dehydrated and dried after purification on a flash column ($SiO_2$— eluent: $CH_2Cl_2$:AcOEt 9:1). 5.4 g (54.7%) of a yellow solid with the following spectral properties are obtained:

$^1$H-NMR (CDCl$_3$): δ (ppm): 8.65 (d, 1H); 8.4 (s, 1H); 7.5 (s, 1H); 7.45 (d, 2H); 7.35 (d, 1H); 3.35 (d, 2H); 3.05 (d, 2H); 2.45 (s, 3H); 2.15 (m, 1H); 1.85 (m, 1H); 1.0 (d, 3H); 0.75 (d, 3H).

Example 6

Synthesis of the 4-methyl-piperazinyl 7-methyl-9-oxo-9H-thioxanthene-3-carboxamide

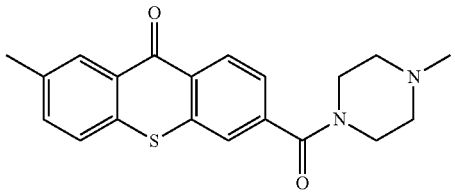

A solution of 3.0 g (31 mmoles) of 4-methyl piperazine and 3.1 g (31 mmoles) of triethyl amine in 40 cc of CH$_2$Cl$_2$ is poured drop by drop in the CH$_2$Cl$_2$ solution containing 7.47 g (25.9 mmoles) of 7-methyl-9-oxo-thioxanthene-3-carbonyl chloride. After approximately 1 hour at room temperature under stirring, the mixture is poured in water, the organic phase is separated and washed again with water. The organic phase is then separated, dehydrated and dried after purification on a flash column (SiO$_2$— eluent: CH$_2$Cl$_2$:AcOEt 9:1) obtaining 4.63 g (50.8%) of a yellow solid, with the following spectral properties:

$^1$H-NMR (CDCl$_3$): δ (ppm): 8.65 (d, 1H); 8.4 (s, 1H); 7.6 (s, 1H); 7.5-7.4 (m, 3H); 3.85 (bs, 2H); 3.45 (bs, 2H); 2.55 (bs, 2H); 2.45 (5, 3H); 2.4 (bs, 2H); 2.3 (s, 3H).

Preparation of 7-methyl-9-oxo-9H-thioxanthene-1-carboxylic acid 28.0 g (0.23 moles) of 4-methylbenzenethiol are dissolved in 180 cc of dimethyl formamide. 14.8 g (0.26 moles) of finely ground potassium hydroxide are added and the solution is stirred at room temperature for half hour.

Then, 48.8 g (0.20 moles) of dimethyl-3-nitrophthalate are added at 75° C. After 3 hours the reaction is complete. After cooling 400 ml of water are added. The organic phase is extracted with diethyl ether, dried and the solvent distilled on a rotary evaporator, then purified by flash chromatography (SiO$_2$— eluent: toluene:AcOEt 8:2) obtaining 1.66 g of a yellow oil. 1.60 g of the yellow oil was dissolved in 120 ml of methanol in presence of 5 g (75.8 mmoles) of potassium hydroxide and stirred under reflux for 1 hour in.

The mixture is cooled and poured in diluted chloridric acid; the organic phase is extracted with diethyl ether. The organic solvent is distilled off obtaining 1.32 g (4.88 mmoles) (90.4%) of 3-(p-tolylthio)benzene-1,2-dicarboxylic acid as a white solid.

The 3-(p-tolylthio)benzene-1,2-dicarboxylic acid is slowly added to 18 g of chlorosulfonic acid cooling at 5 and 10° C. with an ice-bath. After 1 hour the mixture is poured in iced water. The precipitate is filtered, washed with water and dried obtaining 1.20 g (87.7%) of 7-methyl-9-oxo-9H-thioxanthene-1-carboxylic acid as a yellow solid.

$^1$H-NMR (DMSO): δ (ppm): 8.4 (d, 1H); 7.85 (d, 1H); 7.35 (t, 1H); 7.15 (s, 1H); 7.5-7.4 (m, 2H); 2.45 (s, 3H).

Preparation of 7-methyl-9-oxo-9H-thioxanthene-1-carbonyl chloride 0.21 g (0.78 mmoles) of 7-methyl-9-oxo-9H-thioxanthene-1-carboxylic acid are suspended in 30 ml of toluene containing 2 drops of DMF and 0.35 g of thionyl chloride. After stirring for 1 hour at 80° C. the mass is cooled to room temperature obtaining a yellow solution of 7-methyl-9-oxo-9H-thioxanthene-1-carbonyl chloride.

Example 7

Synthesis of N,N-diisobutyl-7-methyl-9-oxo-9H-thioxanthene-1-carboxamide (Comparative)

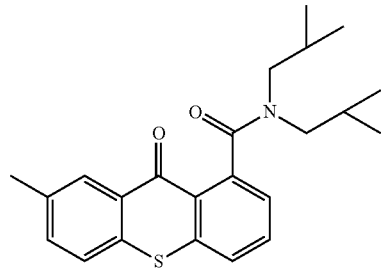 [SMILES: Cc1ccc2sc3cccc(C(=O)N(CC(C)C)CC(C)C)c3c(=O)c2c1]

1.0 g (7.75 mmoles) of diisobutyl amine is dropped into a toluene solution of 7-methyl-9-oxo-9H-thioxanthene-1-carbonyl chloride (0.22 g, 0.78 mmoles). After 2 hours at room temperature under stirring, the mixture is poured in water, the organic phase is separated and washed with water. A crude oil is obtained after evaporation of the solvent. 11.5 mg of a yellow solid are isolated by flash chromatography of the crude oil (SiO$_2$— eluent: CH$_2$Cl$_2$:MeOH 96:4).

$^1$H-NMR (CDCl$_3$): δ (ppm): 8.40 (d, 1H); 7.55 (d, 2H); 7.35 (s, 1H); 7.25 (m, 3H); 3.5 (d, 2H); 3.0 (m, 2H); 2.5 (s, 3H); 2.45-2.3 (m, 1H); 2.0-1.75 (m, 1H); 1.1 (m, 6H); 0.75 (m, 6H).

Example 8

Synthesis of dodecyl 7-methyl-9-oxo-9H-thioxanthene-1-carboxylate (Comparative)

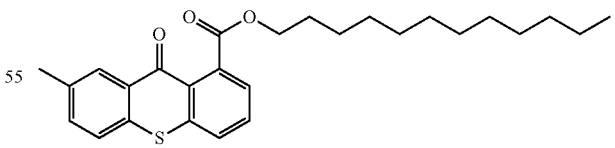

0.43 g (2.31 mmoles) of 1-dodecyl alcohol are added to a toluene solution containing 0.22 g (0.76 mmoles) of 7-methyl-9-oxo-9H-thioxanthene-1-carbonyl chloride. After stirring 1 hour at room temperature, the mixture is poured in water, the organic phase is separated and washed with water. After evaporation of the solvent the oil is purified by flash chromatography (SiO$_2$—eluent: Petroleum Ether:AcOEt 8:2) obtaining 50 mg of a yellow solid.

$^1$H-NMR (CDCl$_3$): δ (ppm): 8.40 (d, 1H); 7.6 (d, 2H); 7.40-7.30 (m, 2H); 4.45 (t, 2H); 2.45 (s, 3H); 1.8-1.7 (m, 2H); 1.5-1.15 (bm, 18H); 0.85 (t, 3H).

Applicative tests.

Evaluation of Formulability Through Solubility in Methylene Chloride.

10 g of the thioxanthone derivatives under investigation are weighed and suspended in the same amount of solvent; the mixture is maintained under stirring at room temperature.

After 2 min the clearness of the solution is evaluated: if the sample is not dissolved further aliquots of solvent are added, keeping the mixture under stirring for two min after each addition until complete solubilization. The results are shown in Table 1.

TABLE 1

| Compound | Solubility |
| --- | --- |
| ITX* | 50% |
| Ex. 4* | 5% |
| Ex. 3* | insoluble |
| Ex. 2* | 33% |
| Ex. 1 | 33% |
| Ex. 5 | 50% |
| Ex. 6 | 5% |

*Comparative

The derivatives of the thioxanthone of the invention turn out to be sufficiently soluble for application as photoinitiators.

Evaluation of the Derivatives of Thioxanthone in a Pigmented Photopolymerizable Composition by Means of FT-IR.

Pigmented photopolymerizable compositions are prepared by mixing 3% by weight of both the photoinitiators of formula I (Examples 1-6) and the coinitiator Esacure A198 (bis-N,N-[4-dimethyl aminobenzoyl)oxyethylen-1-yl]-methylamine), commercialized by Lamberti S.p.A, and up to 100% by weight of a cyan ink for off-set inking.

Isopropyl thioxanthone (ITX) is chosen as reference photoinitiator.

The photopolymerizable compositions are milled with a three cylinders mill (laboratory scale) in order to homogenize the mix and applied with a thickness of 3 μm on a soft polyethylene substrate by means of a film coater (RK Print Coater Instrument Ltd).

The sample, placed in the sample lodgment of a FT-IR (FT-IR 430-Jasco), is exposed to a Mercury/Xenon Vapors light source at high pressure to 120 W/cm (L8868 Light-cure, Hamamatsu) set at a distance of 8 cm from the sample and at an angle of 30°.

IR spectra are acquired at constant time intervals during the photopolymerization and the reduction over time of the peak area at 1408 cm$^{-1}$ assigned to the acrylic double bond was determined by IR software (Perkin Elmer, Spectrum ONE v. 2.0). This allows to quantify the degree of polymerization over the time and therefore the efficiency of the photoinitiator.

The results as % degree of polymerization over the time are reported in Table 2.

TABLE 2

| Compound | % after 1 sec | % after 2 sec | % after 5 sec |
| --- | --- | --- | --- |
| ITX* | 10.0 | 18.9 | 33.0 |
| Ex. 4* | 5.9 | 18.3 | 35.3 |
| Ex. 3* | Insoluble | Insoluble | Insoluble |
| Ex. 2* | 2.5 | 3.1 | 7.2 |
| Ex. 1 | 19.6 | 36.1 | 47.2 |
| Ex. 5 | 18.0 | 33.7 | 45.9 |
| Ex. 6 | 10.0 | 17.2 | 34.1 |

*Comparative

The derivatives of thioxanthone of Examples 1, 5 and 6 have similar or greater effectiveness in comparison with ITX.

The compounds described in the examples were evaluated also as sensitizer in a pigmented composition as described below.

Pigmented photopolymerizable compositions are prepared by mixing 3% by weight of both Esacure 1001 and coinitiator Esacure A 198 (both commercialized by Lamberti S.p.A.), 0.5% by weight of derivatives of thioxanthone of the Examples listed in Table 1 and up to 100% by weight of a cyan ink for off-set inking. ITX is used as reference sensitizer.

The photopolymerizable compositions are milled with a three cylinders mill (laboratory scale) in order to homogenize the mix and applied with a thickness of 3 μm on a soft polyethylene substrate by means of film coater (RK Print Coater Instrument Ltd).

The sample, placed in the sample lodgment of a FT-IR (FT-IR 430-Jasco), is exposed to a Mercury/Xenon Vapors light source at high pressure to 120 W/cm (L8868 Light-cure, Hamamatsu) set at a distance of 8 cm from the sample with an angle of 30°.

IR spectra were acquired at constant time during the photopolymerization and the reduction over the time of the area of the peak at 1408 cm$^{-1}$ assigned to the acrylic double bond is determined with the help of a IR software (Perkin Elmer, Spectrum ONE v. 2.0).

This allows to quantify the degree of polymerization over time and therefore the efficiency of the photoinitiator.

The results as % degree of polymerization over time are reported in Table 3.

The effectiveness as sensitizer of the derivatives of thioxanthone according to the invention is higher or only slightly lower than the effectiveness of ITX.

Evaluation of "Through-Cure"

The "through cure" test evaluates the degree of cross-linking of the deeper layers of the formulate (film) spread on the substrate. The film is considered completely crosslinked when it is not detached from the substrate or damaged by the "thumb twist test". The test is carried out at various speeds of exposure to UV source. The higher the speed the higher the reactivity of the system.

TABLE 3

| Compound | % after 1 sec | % after 2 sec | % after 5 sec |
| --- | --- | --- | --- |
| ITX* | 19.6 | 31.4 | 40.9 |
| Ex. 4* | 20.6 | 33.2 | 43.2 |
| Ex. 3* | Insoluble | Insoluble | Insoluble |
| Ex. 2* | Not reactive | Not reactive | Not reactive |
| Ex. 1 | 17.8 | 29.9 | 40.7 |
| Ex. 5 | 22.3 | 36.7 | 45.8 |
| Ex. 6 | 19.8 | 31.5 | 41.2 |

*Comparative

The products described in the examples were tested both as photoinitiators and sensitizers. For the evaluation as photoinitiator the following formulation is employed (by weight): 3% of derivative of thioxanthone of formula I, 3% of Esacure A 198, up to 100% with cyan ink for off-set printing. For the evaluation as sensitizers the formulation is composed as follows (by weight): 0.5% of derivative of thioxanthone of formula I, 3% of Esacure A 198, 3% of Esacure 1001, up to 100% with cyan ink for off-set printing.

The resulting mixtures are milled with a three cylinders mill (laboratory scale) and applied on a coated cardboard with a thickness of 3 μm by means of film coater (RK Print Coater Instrument Ltd), then exposed at different speed to a mercury vapors lamp at high pressure 120 W/cm.

ITX, in the same amounts, is chosen as reference.

The result are reported in Table 4.

TABLE 4

| Compound | Through-cure (photoinitiator) m/min | Through-cure (sensitizer) m/min |
|---|---|---|
| ITX* | 95 | 60 |
| Ex. 4* | 70 | 60 |
| Ex. 3* | Insoluble | Insoluble |
| Ex. 2* | 5 | Not reactive |
| Ex. 1 | 85 | 53 |
| Ex. 5 | 90 | 60 |
| Es. 6 | 80 | 60 |

*Comparative

The derivatives of the thioxanthone of the invention have an activity comparable to ITX, both as photoinitiators and as sensitizers.

Evaluation of the Extractability in Offset Printing.

The same formulations prepared for the "through cures" (photoinitiator) were applied on coated cardboard with thickness 3 μm (3 g/m²; printed area 71.4 cm²) by means of a film coater (RK Print Coater Instrument Ltd) and exposed to a mercury vapor lamp at high pressure with a power of 160 W/cm at a speed of 30 m/min. After photopolymerization the coated surface is put in contact with another coated cardboard and submitted to a pressure of 20 kg for 10 days at room temperature. At the end of this period the off-set printed cardboard is dipped in 200 mL of a mixture ethanol/water 10/90 or 95/5 and stored for 10 days at the temperature of 40° C.

The amount of derivatives of thioxanthone extracted from the contact solution is determined by means of HPLC (HPLC Method: Column Water Novapak C18, mobile phase in 15 min from 30%/70% Acetonitrile/0.08 M Phosphoric Ac. to 90%/10% Acetonitrile/0.08 M Phosphoric Ac., λ310 nm). Every test was executed in triplicate and the results (mean values) are reported in Table 5.

TABLE 5

| Compound | EtOH 10% | EtOH 95% |
|---|---|---|
| ITX* | 75 ppb | 749 ppb |
| Ex. 4* | <50 ppb | 76 ppb |
| Ex. 1 | <50 ppb | <50 ppb |
| Ex. 5 | <50 ppb | <50 ppb |
| Ex. 6 | <50 ppb | <50 ppb |

*Comparative

The compounds described in examples 1, 5 and 6 do not show migration in the contact solution contrary to both ITX and the compound with a reactive double bond described in Example 4.

Comparison of the reactivity of the 1 and 3 derivatives of thioxanthone by means of Photo DSC.

The compound of Example 1 (dodecyl 7-methyl-9-oxo-9H-thioxanthene-3-carboxylate) and the compound of Example 8 (dodecyl 7-methyl-9-oxo-9H-thioxanthene-1-carboxylate, comparative) were formulated and evaluated by PhotoDSC.

The compound of Example 5 (N,N-diisobutyl-7-methyl-9-oxo-9H-thioxanthene-3-carboxamide) and the compound of Example 7 (N,N-diisobutyl-7-methyl-9-oxo-9H-thioxanthene-1-carboxamide, comparative) were also formulated and compared by PhotoDSC.

The formulations were prepared dissolving in tripropylene glycol diacrylate the compounds described in the Examples 1, 8, 5 and 7 at a concentration of 0.1% w/w and EDB (Ethyl 4-dimethylamino-benzoate) at a concentration of 0.1% w/w.

Photo DSC Test.

About 1 mg of formulation (exactly weighted) was kept into a DSC aluminum panel and analyzed by a Mettler DSC1 calorimeter equipped with a 400 nm LED with a power of 450 mW. The LED was set in order to irradiate the formulation with an intensity of 24.3 mW/cm².

Results

During the exposition to LED at 400 nm the heat developed from the polymerization of formulations prepared with the compounds described in the Examples 1, 8, 5 and 7 was recorded as peak height and peak area (ΔH). The peak height is proportional to the rate of polymerization: higher is the peak—faster is the polymerization.

The results are reported in Table 6.

The comparison of the two formulations obtained with the esters isomers 3 (Example 1) and the ester isomer 1 (Example 8) demonstrate that the isomer 3 is about 1.5 times more reactive than the isomer 1, and the ΔH of the polymerization of isomer 3 is 1.2 higher than the ΔH of the polymerization of isomer 1.

The same effect was observed comparing the two formulations obtained with the amide isomer 3 (Example 5) and amide isomer 1 (Example 7). The amide isomer 3 was 3.5 times more reactive than the amide isomer 1 and the ΔH of amide isomer 3 was about 2 times higher than the ΔH of isomer 1.

TABLE 6

| Compound from Example | Peak height (W/g) | ΔH (peak area) (J/g) |
|---|---|---|
| 1 | 58.9 | 266.4 |
| 8 | 38.4 | 208.5 |
| 5 | 39.0 | 224.8 |
| 7 | 11.1 | 111.4 |

The invention claimed is:

1. A derivative of thioxanthone of formula I

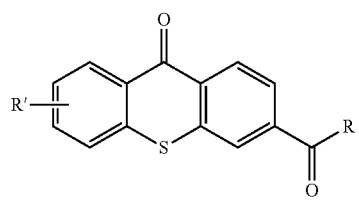

Wherein:
R is OR$_1$ and R$_1$ is a C$_{12}$ linear alkyl chain, and R' is hydrogen or R' is in position 7 and is a methyl group, or
R is NR$_2$R$_3$ and R$_2$ and R$_3$ are isobutyl, and R' is hydrogen or R' is in position 7 and is a methyl group.

2. A photopolymerizable composition comprising:
from 70 to 99.9% by weight at least one photopolymerizable compound, and
from 0.1 to 20% by weight of at least one derivative of thioxanthone of formula I

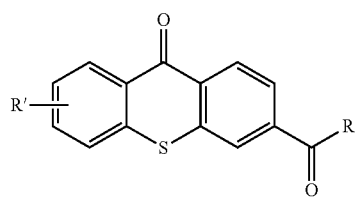

wherein
R is $OR_1$;
R' is hydrogen or a linear or branched alkyl chain having from 1 to 4 carbons ($C_1$-$C_4$);
$R_1$ is a $C_{12}$ linear alkyl chain.

3. A photopolymerizable composition comprising:
from 70 to 99.9% by weight at least one photopolymerizable compound, and
from 0.1 to 20% by weight of at least one derivative of thioxanthone of formula I

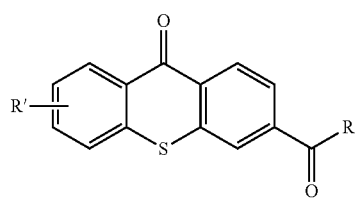

wherein
R is $OR_1$;
R' is hydrogen or R' is in position 7 and is a methyl group;
$R_1$ is a $C_{12}$ linear alkyl chain.

4. A photopolymerizable composition comprising:
from 70 to 99.9% by weight at least one photopolymerizable compound, and
from 0.1 to 20% by weight of at least one derivative of thioxanthone of formula I

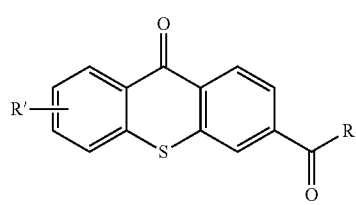

wherein
R is $NR_2R_3$;
R' is hydrogen or a linear or branched alkyl chain having from 1 to 4 carbons ($C_1$-$C_4$);
$R_1$ is a linear or branched alkyl chain having from 8 to 16 carbons ($C_8$-$C_{16}$); and
$R_2$ and $R_3$ are isobutyl groups.

5. A photopolymerizable composition comprising:
from 70 to 99.9% by weight at least one photopolymerizable compound, and
from 0.1 to 20% by weight of at least one derivative of thioxanthone of formula I

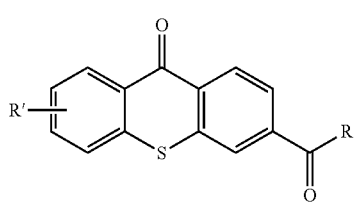

wherein
R is $NR_2R_3$;
R' is hydrogen or R' is in position 7 and is a methyl group;
$R_1$ is a linear or branched alkyl chain having from 8 to 16 carbons ($C_8$-$C_{16}$); and
$R_2$ and $R_3$ are isobutyl groups.

6. A photopolymerizable composition comprising:
from 70 to 99.9% by weight at least one photopolymerizable compound, and
from 0.1 to 20% by weight of at least one derivative of thioxanthone of formula I

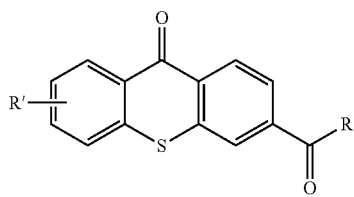

wherein
R is $OR_1$, $SR_1$ or $NR_2R_3$;
R' is hydrogen or a linear or branched alkyl chain having from 1 to 4 carbons ($C_1$-$C_4$);
$R_1$ is a linear or branched alkyl chain having from 8 to 16 carbons ($C_8$-$C_{16}$)
$R_2$ and $R_3$ are:
linear or branched alkyl chains that are the same or different and having from 4 to 8 carbons ($C_4$-$C_8$), or
combined in order to form a 5 or 6 member ring which may be substituted and have up to two heteroatoms; and
the photopolymerizable composition further comprises a coinitiator which is (bis-N,N-[4-dimethylaminobenzoyl)oxyethylen-1-yl]-methylamine).

* * * * *